United States Patent
Negus et al.

[11] Patent Number: 6,113,587
[45] Date of Patent: *Sep. 5, 2000

[54] HANDPIECE FOR A MEDICAL LASER SYSTEM

[75] Inventors: Charles C. Negus, Taunton; Robert I. Rudko, Holliston; Stephen J. Linhares; Stephen M. Perez, both of Taunton, all of Mass.

[73] Assignee: PLC Medical Systems, Inc., Franklin, Mass.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/190,950

[22] Filed: Feb. 3, 1994

Related U.S. Application Data

[63] Continuation-in-part of application No. 08/014,363, Feb. 5, 1993, abandoned, which is a continuation of application No. 07/928,531, Aug. 13, 1992, abandoned, which is a continuation of application No. 07/586,891, Sep. 24, 1990, abandoned.

[51] Int. Cl.[7] .................................................... A61B 18/18
[52] U.S. Cl. .................................. 606/14; 606/13; 606/17
[58] Field of Search ........................... 606/2–5, 7, 10–18, 606/1, 182, 167, 19; 219/121.6, 121.62; 604/115, 164, 174; 128/763, 395–398; 607/88, 89; 600/108

[56] References Cited

U.S. PATENT DOCUMENTS

| | | | |
|---|---|---|---|
| 1,135,465 | 4/1915 | Pollock | 606/182 |
| 1,562,460 | 11/1925 | Fee | 606/49 |
| 2,823,677 | 2/1958 | Hein et al. | 606/182 |
| 3,756,242 | 9/1973 | Coss | 606/167 |
| 3,865,113 | 2/1975 | Sharon et al. | 606/18 |
| 3,913,582 | 10/1975 | Sharon | 606/10 |
| 4,266,548 | 5/1981 | Davi | 606/17 |
| 4,757,515 | 7/1988 | Hughes | 372/109 |
| 4,850,352 | 7/1989 | Johnson | 606/13 |
| 4,940,411 | 7/1990 | Vassiliadis et al. | 606/3 X |

FOREIGN PATENT DOCUMENTS 0153908  12/1980  Japan ........................................ 606/17

Primary Examiner—Michael Peffley
Attorney, Agent, or Firm—Iandiorio & Teska

[57] ABSTRACT

A handpiece for a medical laser system comprising a barrel for having a passage for transmitting a laser beam and a contacting wall on one end of said barrel including an aperture in communication with the passage, a solid face extending radially outward from the aperture to the periphery of said contacting wall, and a knurled surface on the face for preventing movement of the contacting wall with respect to the heart wall during surgery.

19 Claims, 3 Drawing Sheets

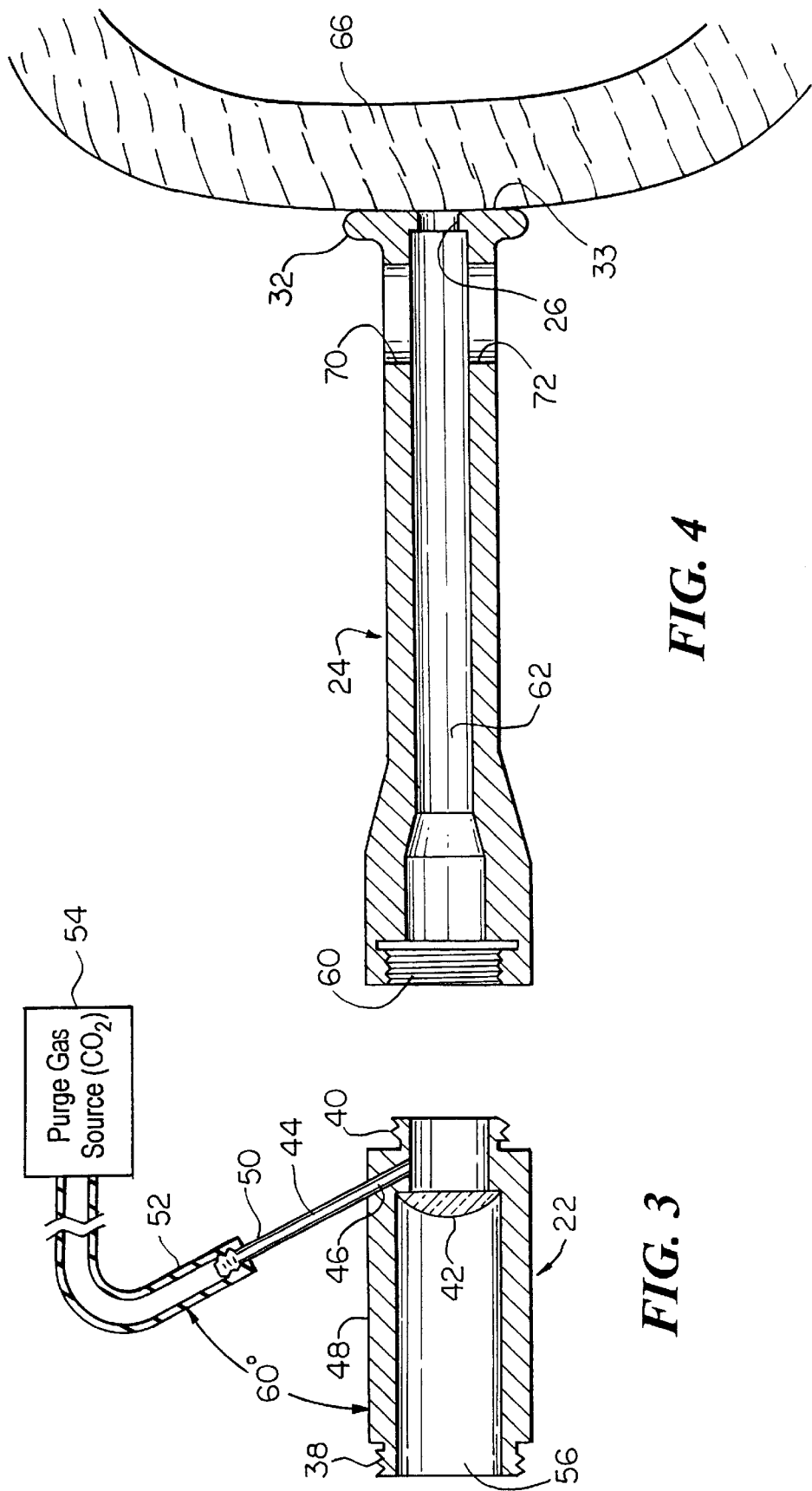

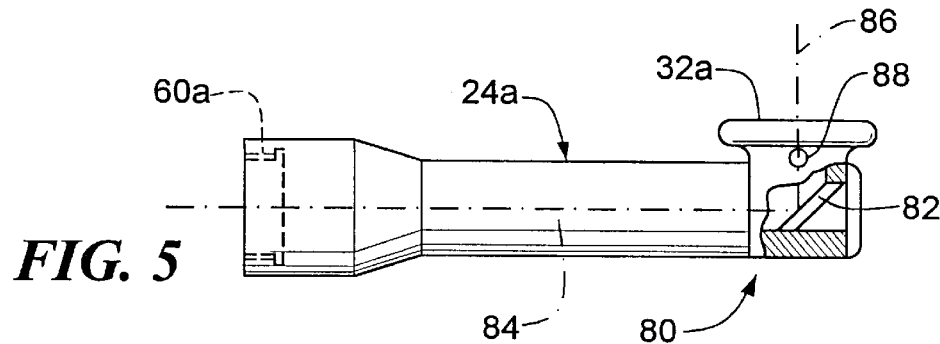
*FIG. 5*
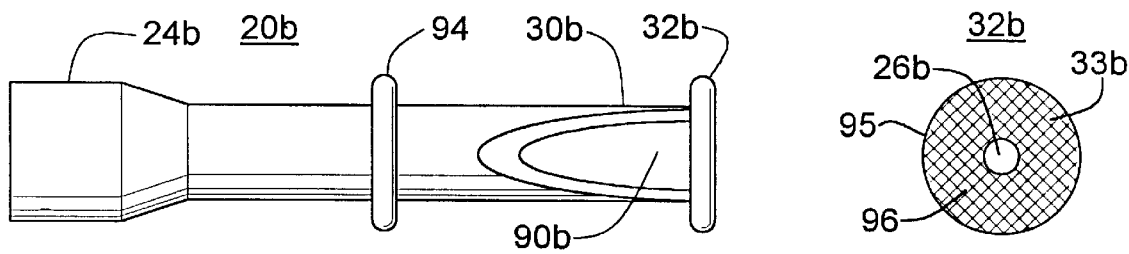
*FIG. 6*  *FIG. 8*
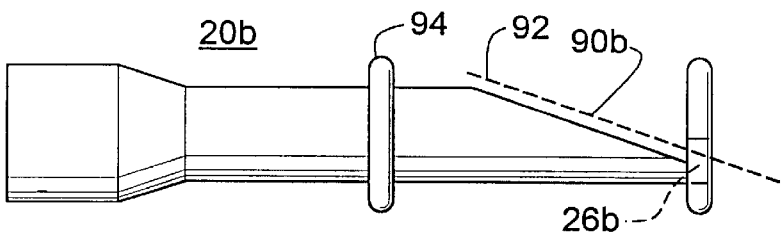
*FIG. 7*
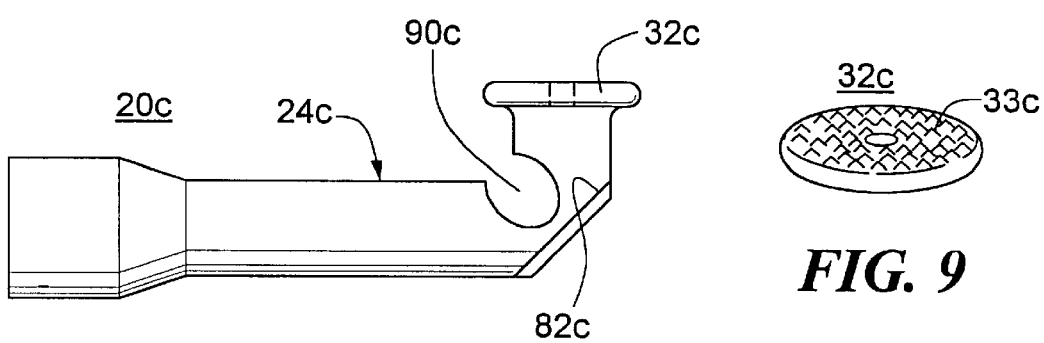
*FIG. 10*  *FIG. 9*

HANDPIECE FOR A MEDICAL LASER SYSTEM

RELATED CASES

This application is a continuation-in-part application of Ser. No. 08/014,363 filed Feb. 5, 1993 (now abandoned) which is a continuation of Ser. No. 07/928,531 filed Aug. 13, 1992 (now abandoned) which is a continuation of Ser. No. 07/586,891 filed Sep. 24, 1990 (now abandoned). This application incorporates herein by reference the following applications having common inventors and assignee: application Ser. No. 07/586,885 filed Sep. 24, 1990 issued as U.S. Pat. No. 5,109,388 and application Ser. No. 07/586,951 filed Sep. 24, 1990 issued as U.S. Pat. No. 5,125,926.

FIELD OF INVENTION

This invention relates to a handpiece for a medical laser system such as a transmyocardial re-vascularization laser system, and more particularly to such a handpiece whose contact surface avoids destabilization of the beating heart.

BACKGROUND OF INVENTION

Transmyocardial revascularization (TMR) is an alternative technique to bypass surgery for increasing blood flow to the heart muscle. TMR involves puncturing the heart wall with a laser to form a plurality of holes which heal on the outside but remain open on the inside of the heart to provide an alterative source of blood to the heart muscle. This technique has been employed on a stilled, by-passed heart using a $CO_2$ laser with a hand-piece which rests on the heart. Recently, a dramatic improvement in TMR has enabled this technique to be used on a beating heart without the need to slow or still it. This has been accomplished with an innovative synchronizing approach disclosed in U.S. Pat. Nos. 5,125,926 and 5,109,388 incorporated herein by reference. However, this has introduced new problems. A beating heart is electrically active and the contact of a handpiece against the heart wall may disrupt that electrical activity and interfere with the heart function. Arrhythmia and fibrillation can occur and can result in heart failure. Further, any interference with the electrical field of the heart interrupts the synchronous operation of the laser so that the laser is no longer constrained to fire at the optimum moment in the beating heart cycle. The current handpiece used with $CO_2$ lasers have a relatively sharp tip on a gauge rod extending from the end of the handpiece used to consistently position the handpiece at the proper distance from the stilled heart wall for accurate laser beam focusing and impingement. Such a tip creates increased pressure on the heart, which can cause arrhythmia, fibrillation, and can even puncture the wall of the heart. Further, with these handpieces it is difficult to maintain the laser beam perpendicular with the wall of a beating heart as is necessary to effect clean, correctly placed holes in the heart wall. Finally, these handpieces may slide on the heart wall during the procedure disrupting the surgeon's concentration.

SUMMARY OF INVENTION

It is therefore an object of this invention to provide an improved laser handpiece for a laser system for transmyocardial vascularization.

It is a further object of this invention to provide such a laser handpiece which more readily maintains perpendicularity with the wall of a beating heart.

It is a further object of this invention to provide such a laser handpiece which accurately locates the laser beam focal point at the correct point on the heart wall.

It is a further object of this invention to provide such a laser handpiece which reduces interference with the heart electric field and function.

It is a further object of this invention to provide such a laser hand piece which dissipates the laser plume to prevent interference with or damage to the laser beam lens.

It is a further object of this invention to provide such a laser handpiece which prevents movement of the handpiece with respect to the heart wall.

This invention results from the realization that an effective and safe handpiece capable of contacting the wall of a beating heart to insure proper location and focus of the laser beam, yet minimize danger to or interference with the beating heart, can be achieved by focusing the laser beam in the vicinity of the laser beam exit aperture at the end of the handpiece and providing a large, flat, knurled heart contact surface at the end of the handpiece to minimize pressure on and interference with the beating heart and also to prevent movement of the contact surface with respect to the heart.

This invention features a handpiece for use in a medical laser system such as a transmyocardial revascularization heart-synchronized pulsed laser system as disclosed in U.S. Pat. No's. 5,125,926 and 5,109,388.

The handpiece includes a barrel having a passage for transmitting a laser beam. A contacting wall is located on one end of the barrel to be positioned against the heart wall. The contacting wall includes an aperture in communication with the laser beam passage in the barrel. The contacting wall includes a solid face extending radially outward from the aperture to the periphery of the contacting wall providing a broad, flat contact surface for the handpiece which does not interfere with the function of the heart during the medical procedure and which stabilizes the handpiece on the heart wall. The contacting wall includes a knurled surface for preventing movement of the contacting wall with respect to the heart wall during surgery.

The barrel may include a window proximate the contacting wall and a finger grip along the length thereof to assist the surgeon in viewing the lasing site and to provide a firm grip during surgery.

The barrel may be straight or angled and include reflecting means such as a mirror. Also, a lens focusing unit may be included to focus the laser beam proximate the aperture, beyond the aperture, within the barrel, or in the aperture.

DISCLOSURE OF PREFERRED EMBODIMENT

Other objects, features and advantages will occur to those skilled in the art from the following description of a preferred embodiment and the accompanying drawings, in which:

FIG. 3 is an enlarged cross-sectional view of the focusing lens assembly incorporated with the handpiece of FIGS. 1 and 2;

FIG. 4 is an enlarged sectional view of the barren of the handpiece of FIGS. 1 and 2;

FIG. 5 is a side elevational view with portions broken away of an alternative form of barrel similar to that shown in FIG. 4;

FIG. 6 is a top view of another embodiment of the handpiece according to this invention;

FIG. 7 is a side view of the handpiece of FIG. 6;

FIG. 8 is an end view of the contacting wall of the barrel of FIG. 6 showing the knurled surface;

FIG. 9 is a schematic three-dimensional view of another embodiment of the knurled contacting wall for the handpiece according to this invention; and FIG. 10 is a sideview of an angled barrel for a handpiece according to this invention.

The handpiece of this invention for use in a transmyocardial revascularization heart-synchronized pulsed laser system may be accomplished using a barrel having a passage for transmitting a laser beam. The barrel may be simply a hollow tube. There is a surface at the distal end of the barrel for contacting the wall of the heart. This surface is broad and flat so that there are no sharp points to probe or prick the heart wall. This shape also minimizes the contact pressure between the handpiece and the heart wall and minimizes interference with the operation of the heart muscle and the electrical activity of the beating heart. The handpiece, at least at its contact surface, is electrically and thermally insulating for the same purpose. There is an aperture located at the distal end of the barrel in the enlarged surface for transmitting a laser beam through to the heart wall. There are also some means for focusing the laser beam proximate to the aperture to vaporize the tissue of the heart wall and create a hole through the wall to the interior of the heart chamber. The means for focusing is typically a lens which is mounted in a focusing unit or lens unit associated with the barrel.

The laser may be focused at, near or beyond the aperture. There is an inlet to introduce a purging gas through the passage to purge the aperture and the means for focusing of debris produced by the vaporization of the heart wall by the laser beam. There is one or more outlets proximate the distal end of the barrel through which the purged gas with the debris is vented. The barrel may be straight or may be angled. If it is angled, there are suitable deflecting means such as mirrors or reflectors, to redirect the beam along the angled or curved barrel. The contacting wall is knurled for preventing movement of the contacting wall with respect to the heart wall during surgery. By "knurled" is meant any frictional surface.

Figure 1:
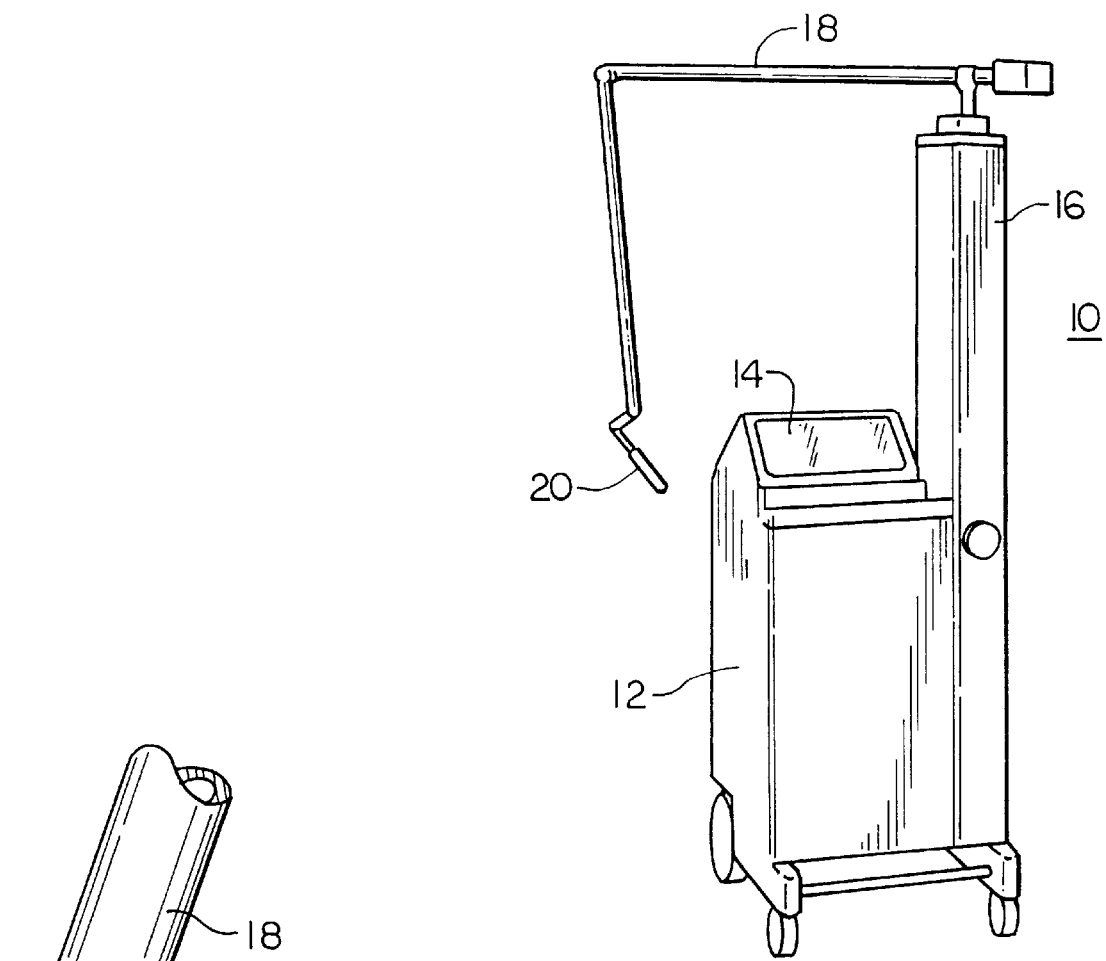
FIG. 1 is a three-dimensional view of a $CO_2$ surgical laser system employing the handpiece of this invention.
Figure 2:
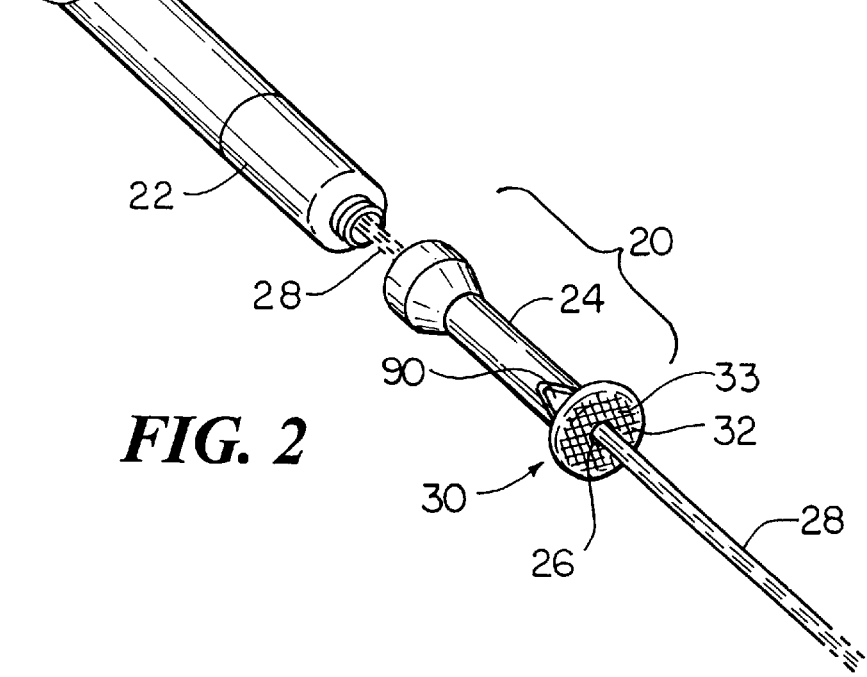
FIG. 2 is an enlarged view of a handpiece according to this invention and a portion of the articulated optical arm which carries it.

There is shown in FIG. 1 a surgical laser system 10 including a power supply 12 and control panel 14 for operating $CO_2$ laser 16, whose output beam is directed through articulated arm 18 to handpiece 20. Handpiece 20, FIG. 2, may be connected to lens unit 22 including a lens for focusing the laser beam. Barrel 24 of handpiece 20 includes an aperture 26 through which the laser beam 28 exits. The distal end 30 of barrel 24 includes an enlarged knurled contacting wall 32 for contacting the wall of the heart to be perforated by the laser beam. Contacting wall 32 is relatively large to minimize the contact pressure between it and the heart wall, and is flat with rounded edges to minimize interference with the heart. Contacting wall 32 includes knurled surface 33 for preventing movement of contacting wall 32 with respect to the heart wall during surgery. Contacting wall 32 is typically 1 cm or greater in diameter, and may be electrically and thermally insulating.

Window 90 allows the surgeon to view the lasing site and also serves to vent gasses and vapor. Focusing unit or lens unit 22, FIG. 3, includes a threaded portion 40 which interconnects with barrel 24 of handpiece 20. Carried within unit 22 is focusing lens 42. An inlet tube 44 is joined by interference fit with bore 46 and a cylindrical wall 48 of unit 22. At its free end 50, inlet 44 is connected to a hose 52 which is in turn connected to a purge gas source 54 which provides a gas such as $CO_2$ under gentle pressure to create a backflow from lens 42 forward into barrel 24. This keeps any debris from the vaporization from contacting and obscuring or damaging lens 42. Lens 42 is positioned directly in line with passage 56 provided in unit 22 for propagation of the laser beam. Threads 40 of lens unit 22 engage with threads 60 of barrel 24, FIG. 4, which also includes a passage 62 which communicates with laser aperture 26 to create a clear passage for the propagation of laser beam 28 to wall 66 of a beating heart. Other connection means may be used to engage lens unit 22 with barren 24 such as snap on, or turn and lock type connections. Lens 42 focuses the laser beam 28 proximate aperture 26 and surface 32.

As can be seen clearly in FIG. 4, contacting wall 32 of handpiece 20 is considerably broader than the cross-sectional area of barrel 24 alone and is formed in the shape of a flange with knurled surface 33 being relatively flat and all the edges rounded. This increases the area of contact with the heart and therefore decreases the pressure of force per unit area on the heart. It also provides a more stable platform by which to maintain perpendicularity between the beam 28 and the heart wall 66. Thus, this construction provides the necessary precision in locating the focus of the beam on the heart wall without interfering with the heart operation or its electrical activity. Barrel 24 may include vent holes 70, 72 for exhausting the purging gas and trapped debris away from the lens 42 and away from aperture 26.

Although handpiece 20 has been shown with barrel 24 as a straight member, this is not a necessary limitation of the invention. For example, barrel 24a, FIG. 5, may include a right angle configuration 80, so that contacting wall 32a is facing at a right angle to the path of the laser beam. A reflective surface 82 is provided to reflect the beam from an incoming path parallel to axis 84 to the outgoing path parallel to axis 86. One or more vent holes 88 may be provided for exhausting gas. Angles other than a right angle are possible for barrel 24a.

In another embodiment, handpiece 20b, FIG. 6 includes barrel 24b with contacting wall 32b on distal end 30b of barrel 24b. Window 90b is proximate contacting wall 32b for vapor release and also so that surgeon can view the site being lased. As shown in FIG. 7, the surgeon has a clear view of the lasing site proximate aperture 26b through window 90b along axis 92. Raised rim 94 on barrel 24b provides a finger grip for the surgeon to assist in gripping barrel 24b.

Contacting wall 32b, FIG. 8, includes knurled surface 33b formed by cross hatching surface 33b as shown, while in another embodiment, contacting wall 32c, FIG. 9, includes knurled surface 33c consisting of a series of raised ridges. Other surface patterns are possible and are within the scope of this invention. And, although the entirety of wall 32b has the rough "knurled" appearance, this is not a limitation of the present invention since only half, or some other portion may be knurled. Contacting wall 32b, FIG. 8, includes solid face 96 which extends continuously radially outward from aperature 26b to the periphery 95 of contacting wall 32b.

Right angled barrel 24c of handpiece 20c, FIG. 10 includes contacting wall 32c facing at a right angle to the path of the laser beam. Reflective surface 82c, such as a mirror, reflects the beam as discussed with reference to FIG. 5. Window 90c is provided for cleaning reflective surface 82c and provides an aperature from which purge gasses and debris are evacuated from barren 24c.

In a preferred embodiment, the handpiece is manufactured from a medical grade acrylic and is injection molded to form the different barren shapes.

Although specific features of the invention are shown in some drawings and not others, this is for convenience only as each feature may be combined with any or all of the other features in accordance with the invention.

And other embodiments will occur to those skilled in the art and are within the following claims:

What is claimed is:

1. A handpiece for use in a medical laser system comprising:
   a barrel having a passage for transmitting a laser beam; and
   a contacting wall at one end of said barrel, the contacting wall including an aperture in communication with said passage and a face extending continuously radially outward from said aperture to the periphery of said contacting wall, the face including a knurled portion.

2. The handpiece of claim 1, the handpiece being adapted for focusing a laser beam transmitted through said passage to focus the laser beam proximate said aperture to vaporize the tissue of the heart wall and create a hole therein.

3. The handpiece of claim 2 wherein the handpiece focuses the laser beam beyond said contacting wall.

4. The handpiece of claim 2 wherein the handpiece focuses the laser beam within said barrel.

5. The handpiece of claim 2 wherein the handpiece focuses the laser beam in said aperture.

6. The handpiece of claim 1 in which said contacting wall is broader in cross-sectional area than said barrel and said contacting wall is flat with all the edges rounded.

7. The handpiece of claim 1 further including means for introducing a gas to purge said passage of debris from the vaporized heart wall.

8. The handpiece of claim 7 further including exhaust means in communication with said passage for venting debris purged by the gas.

9. The handpiece of claim 7 in which said exhaust means is located proximate said aperture.

10. The handpiece of claim 1 in which said barrel is straight.

11. The handpiece of claim 1 in which said contacting wall is thermally insulating.

12. The handpiece of claim 1 in which said barrel is angled and includes deflecting means for directing a laser beam along the angled barrel.

13. The handpiece of claim 12 in which said deflecting means includes a mirror.

14. A handpiece for use in a medical laser system comprising:
   a barrel having a passage for transmitting a laser beam; a contacting wall at one end of said barrel including an aperture in communication with said passage and a knurled face extending continuously radially outward from said aperture to the periphery of said contacting wall; and
   means for focusing a laser beam proximate said aperture to vaporize the tissue of the heart wall and create a hole therein.

15. The handpiece of claim 14 in which said contacting wall includes a solid face.

16. The handpiece of claim 14 in which said contacting wall is flat with all the edges rounded.

17. A handpiece for use in a medical laser system comprising:
   a barrel having an internal passage for transmitting a laser beam; and
   a contacting wall extending transversely from one end of said barrel, said contacting wall having an aperture in communication with said passage of said barrel, said contacting wall having a face extending continuously radially outward from said aperture to the periphery of said contacting wall, the face having a knurled portion.

18. A handpiece for use in a transmyocardial revascularization heart synchronized pulsed laser system, the handpiece comprising:
   a barrel having an internal passage for transmitting a laser beam; and
   a contacting wall at one end of said barrel including an aperture in communication with said passage and a knurled face extending continuously radially outward from said aperture to the periphery of said contacting wall such that the combination of the barrel and the contacting wall acts as a handpiece for contacting a beating heart during use of a transmyocardial revascularization heart synchronized pulsed laser system.

19. A handpiece for a medical laser system comprising:
   a barrel portion having a passage for transmitting a laser beam; and
   a knurled contacting wall on one end of the barrel, the contacting wall having a periphery, an aperture in the contacting wall smaller than the passage of the barrel, the contacting wall including a solid face extending continuously radially outward from the aperture to the periphery of the contacting wall, the periphery of the contacting wall extending beyond the barrel portion forming a flange on the end of the barrel to provide a stable platform by which to maintain perpendicularity of the handpiece on a heart during surgery and to disperse the pressure imposed by the handpiece on a heart wall during surgery.

* * * * *